(12) United States Patent
Day et al.

(10) Patent No.: US 9,813,003 B2
(45) Date of Patent: Nov. 7, 2017

(54) APPARATUS WITH A MAIN CONTROL UNIT, A CONTROL UNIT AND AN ELECTROMECHANICAL DEVICE AND A METHOD FOR OPERATING SUCH AN APPARATUS

(71) Applicant: SANOFI-AVENTIS DEUTSCHLAND GMBH, Frankfurt am Main (DE)

(72) Inventors: Shane Alistair Day, Warwickshire (GB); Barry Yates, Warwickshire (GB); Aidan Michael O'Hare, Coventry (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 625 days.

(21) Appl. No.: 14/367,458

(22) PCT Filed: Dec. 21, 2012

(86) PCT No.: PCT/EP2012/076771
§ 371 (c)(1),
(2) Date: Jun. 20, 2014

(87) PCT Pub. No.: WO2013/093059
PCT Pub. Date: Jun. 27, 2013

(65) Prior Publication Data
US 2015/0303851 A1 Oct. 22, 2015

(30) Foreign Application Priority Data
Dec. 22, 2011 (EP) .................................. 11195220

(51) Int. Cl.
*H02P 8/34* (2006.01)
*A61M 5/19* (2006.01)
(Continued)

(52) U.S. Cl.
CPC ........... *H02P 8/34* (2013.01); *A61M 5/14212* (2013.01); *A61M 5/14546* (2013.01);
(Continued)

(58) Field of Classification Search
CPC ........................................................ H02P 8/34
(Continued)

(56) References Cited

U.S. PATENT DOCUMENTS 533,575 A 2/1895 Wilkens
4,908,017 A 3/1990 Howson et al.
(Continued)

FOREIGN PATENT DOCUMENTS

EP 0518630 A2 12/1992
EP 0937471 A2 8/1999
(Continued)

OTHER PUBLICATIONS

Communication Pursuant to Article 94(3) EPC issued in European Patent Application No. 12808406.8 dated Dec. 14, 2015.
(Continued)

*Primary Examiner* — David S Luo
(74) *Attorney, Agent, or Firm* — McDonnell Boehnen Hulbert & Berghoff LLP

(57) ABSTRACT

The invention relates to an apparatus comprising an electromechanical device, a control unit, a main control unit and a motion detector, wherein said control unit is configured to control said electromechanical device. The invention also relates to a method for operating an apparatus with a main control unit, a control unit and an electromechanical device. The technical problem of providing an apparatus with an electromechanical device, the reliability of which is improved, is solved by an apparatus wherein the main control unit is configured to provide information to the control unit. The motion detector and the main control unit (Continued)

are configured such that information about the movement of the electromechanical device is provided by the motion detector at least to the main control unit. The technical problem is also solved by a method for operating an apparatus, in particular an apparatus or medical device according to the invention.

18 Claims, 5 Drawing Sheets

(51) Int. Cl.
  *A61M 5/24* (2006.01)
  *A61M 5/30* (2006.01)
  *A61M 5/142* (2006.01)
  *A61M 5/172* (2006.01)
  *A61M 5/145* (2006.01)
  *A61M 5/168* (2006.01)

(52) U.S. Cl.
  CPC .... *A61M 5/16804* (2013.01); *A61M 5/16827* (2013.01); *A61M 5/172* (2013.01); *A61M 5/19* (2013.01); *A61M 5/2448* (2013.01); *A61M 5/30* (2013.01); *A61M 2205/103* (2013.01); *A61M 2205/17* (2013.01); *A61M 2205/3306* (2013.01); *A61M 2205/3365* (2013.01)

(58) Field of Classification Search
  USPC .......................................... 318/696, 34, 558
  See application file for complete search history.

(56) References Cited

U.S. PATENT DOCUMENTS

| | | | |
|---|---|---|---|
| 5,130,543 A * | 7/1992 | Bradbeer | G01S 1/70 250/342 |
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,241,704 B1 * | 6/2001 | Peterson | A61M 5/14228 604/31 |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 7,385,363 B2 * | 6/2008 | Schemm | H02K 41/031 318/135 |
| 7,599,758 B2 * | 10/2009 | Reindle | A47L 9/2821 15/3 |
| 8,965,707 B2 * | 2/2015 | Blomquist | G06F 19/3406 702/19 |
| 9,457,140 B2 | 10/2016 | Barron et al. | |
| 2002/0022807 A1 | 2/2002 | Duchon et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2009/0275916 A1 | 11/2009 | Harms et al. | |

FOREIGN PATENT DOCUMENTS

| | | |
|---|---|---|
| EP | 0937476 A2 | 8/1999 |
| EP | 1688846 A1 | 8/2006 |
| JP | 2009516577 A | 4/2009 |
| KR | 20090027301 A | 3/2009 |
| WO | 9938554 A1 | 8/1999 |
| WO | 0110484 A1 | 2/2001 |
| WO | 2011117404 A2 | 9/2011 |

OTHER PUBLICATIONS

English Translation of Notice of Reasons for Rejection issued in Japanese Patent Application No. 2014-548089 dated Sep. 20, 2016.

* cited by examiner

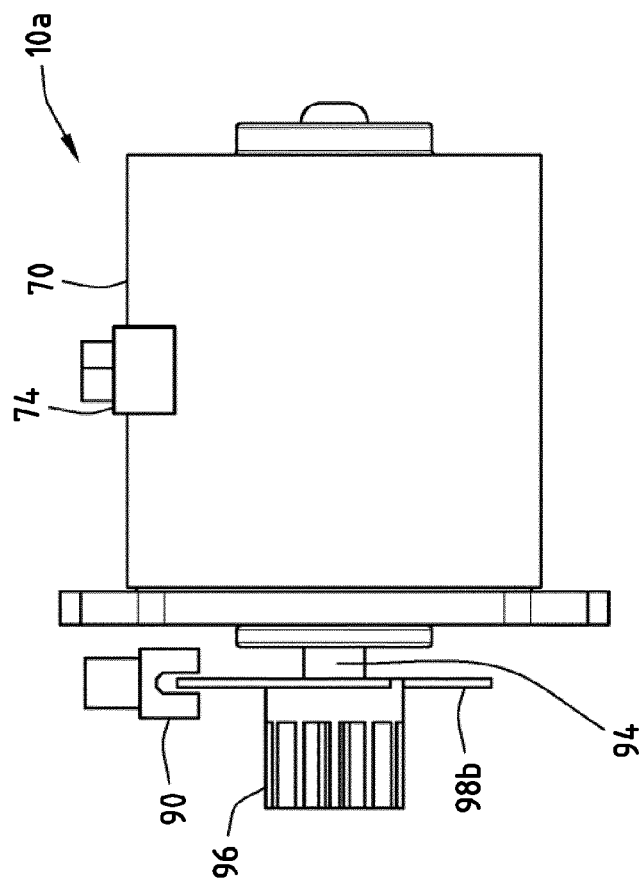
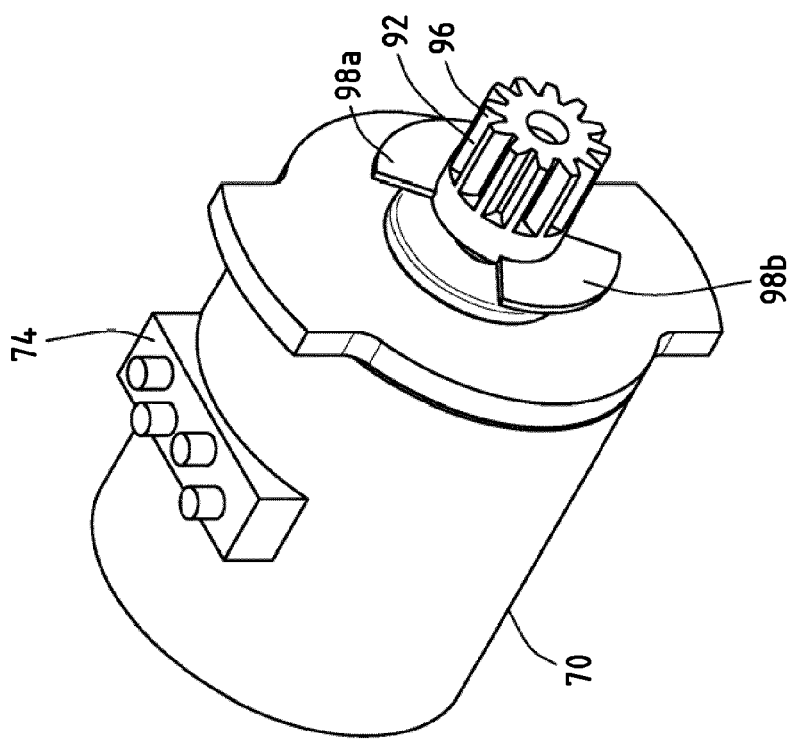
Fig.5b
Fig.5a

APPARATUS WITH A MAIN CONTROL UNIT, A CONTROL UNIT AND AN ELECTROMECHANICAL DEVICE AND A METHOD FOR OPERATING SUCH AN APPARATUS

CROSS REFERENCE TO RELATED APPLICATIONS

The present application is a U.S. National Phase Application pursuant to 35 U.S.C. §371 of International Application No. PCT/EP2012/076771 filed Dec. 21, 2012, which claims priority to European Patent Application No. 11195220.6 filed Dec. 22, 2011. The entire disclosure contents of these applications are herewith incorporated by reference into the present application.

FIELD OF INVENTION

The invention relates to an apparatus comprising an electromechanical device, a control unit, a main control unit and a motion detector, wherein said control unit is configured to control said electromechanical device. The invention also relates to a method for operating an apparatus with a main control unit, a control unit and an electromechanical device.

BACKGROUND

It is known from the state of the art to use electromechanical devices to provide a mechanical movement by means of electrical energy, for example. It is also known to monitor such mechanical movements with motion detectors. This can increase the assurance that a specific movement of the electromechanical device has indeed happened as requested by a control unit. This reduces the probability of unregistered errors of devices in which such electromechanical devices are used. Here, an error would mean that the electromechanical device is not moving although a control signal was sent by the control unit, or that the electromechanical device moves without a command from the control unit, for example. It is disadvantageous though that in order to quickly detect any errors during the movement of the electromechanical device the control unit is faced with additional computational work load. Since there are usually plenty of tasks to be handled by the control unit, a reliable detection of errors or malfunctions may not be guaranteed. Moreover, in case of a malfunctioning control unit the detection of the actual movement by a motion detector cannot be analyzed reliably. Furthermore, in case of a software malfunction, a check of the information provided by the motion detector may not be sufficient either to provide reliable error detection.

SUMMARY

There are numerous reasons why an electromechanical device would not follow the control signal. There may be malfunctions or the load on the mechanical device may be too large for the electromechanical device to move in the expected way. Especially to overcome the latter problem, it is possible, for example, to over engineer such systems and provide an electromechanical device, which is in every case strong enough to carry the load. On the down side, this may result in higher costs and a higher consumption of energy and space.

Especially for stepper motors, there is the problem of so called slipping and stalling. If the stepper motor slips a step, it does not perform a single step even though a control signal for the step was sent. In an extreme case, the stepper motor is stalling. Then the load is too high and the stepper motor does not only slip a step but does not move at all.

In plenty of applications, especially in the field of medical devices, it is of utmost importance to provide a device which has a very low fail rate and which is insusceptible to errors and malfunctioning. This is especially the case for portable devices, which are moved around and especially prone to errors due to jolts etc.

In the case of a medical device, the device may be capable of delivering one or more drug agent. For example, the device may be capable of delivering at least two drug agents from separate reservoirs. Such drug agents may comprise a first and a second medicament. The medical device includes a dose setting mechanism for delivering the drug agents automatically or manually by the user.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent.

The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the microprocessor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

In view of the aforementioned, the invention faces the technical problem of providing an apparatus with an electromechanical device with improved reliability.

The technical problem is solved by an apparatus wherein the main control unit is configured to provide information to the control unit. The motion detector and the main control unit are configured such that information about the movement of the electromechanical device is provided by the motion detector at least to the main control unit.

By providing, additionally to the control unit, a main control unit, to which information about the movement of the electromechanical device is provided, an improved reliability of the apparatus can be provided. The control unit can be seen as a dedicated control unit for the specific electromechanical device, mainly or exclusively entrusted with the control of the electromechanical device. On the one hand, the main control unit can send information such as relevant movement instructions to the control unit, which control unit in turn can instruct the electromechanical device. On the other hand, the main control unit gets feedback about the actual mechanical movement of the electromechanical device and the main control unit can initiate counter measures, for example, in case a mismatch between the information sent by the main control unit and received from the motion detector is detected.

Such counter measures may be further instructions to the control unit, if the actual mechanical movement of the electromechanical device is less than instructed by the main control unit and/or the control unit. A counter measure may also be the immediate stop of the electromechanical device.

Another possibility is to provide a warning to the user via optical, acoustical or other perceivable signals. Such a warning can also be provided together with the initiation of counter measures.

Also, due to the separated responsibilities of controlling or driving the motor by the control unit and supervising the control unit and the electromechanical device by the main control unit, an improvement in reliability is provided. A malfunctioning control unit is in this way still easily detectable by the main control unit.

An electromechanical device can be any electrically driven motor, for example a brushless DC motor providing a continuous movement or a stepper motor providing a discrete movement.

The control unit and the main control unit can in particular be realized with microprocessors. The control unit can in particular be a motor driver. Such a motor driver can in particular include an H-bridge to control a stepper motor, for example. The H-bridge can also be provided separately.

A motion detector in the sense of the application is any device that is able to provide qualitative and / or quantitative information or feedback about the mechanical movement of the electromechanical device. This can be realized by any sort of encoder being able to transform information of mechanical movement into electrical signals, like rotary or linear encoders.

The electromechanical device, the control unit and the motion detector are in particular a first electromechanical device, a first control unit and a first motion detector, since further such devices and/or units and/or detectors can be provided in embodiments of the apparatus according to the invention.

According to an embodiment of the apparatus according to the invention, the motion detector is configured to provide information to the control unit. Additionally to providing information about the movement of the electromechanical device to the main control unit, information of the motion detector is also provided to the control unit. This provides an additional feedback route to prevent the apparatus from malfunctioning. In this case, the control unit is for example able to perform a comparative operation between the information, for example in form of a control signal, sent to the electromechanical device and the information provided by the motion detector. This is advantageous, since a quick feedback can be provided to the control unit and counter measures correcting the electromechanical device or stopping the electromechanical device can be quickly provided to the electromechanical device without first being processed by the main control unit. At the same time though, the main control unit maintains the ability to overrule instructions by the control unit, for example by disconnecting the control unit and electromechanical device, by suppressing commands from the control unit to the electromechanical device, by disabling the power supply to the electromechanical device or by halting the control unit's issuing of signals to the electromechanical device.

In this way a first closed feedback control is provided between control unit, electromechanical device and motion detector. At the same time the second closed feedback between the main control unit, the control unit, the electromechanical device and the motion detector is maintained. This provides an especially safe error detection of the apparatus.

A further advantage of this embodiment is that in case of a software or hardware malfunction either in the sphere of the control unit or in the sphere of the main control unit a corrective action, a preventive action or an intervention of the other unit can be initiated.

If the main control unit is configured to control a switch to disconnect the control unit from the electromechanical device, the prevention of harmful or destructive consequences can be further improved. This switch is in particular arranged between the control unit and the electromechanical device in order to easily interrupt the connection there between. A switch can be any sort of electrical or mechanical element able to intervene in the connection between the control unit and the electromechanical device, such as transistors or circuit breakers. That means, that the connection can either be interrupted completely or instead a connection between the main control unit and the electromechanical device can be established overriding the control unit, for example. Such a switch provides a more secure technique to prevent further consequences than a software based technique, for example.

Alternatively the main control unit is configured to control a switch to disconnect at least an H-bridge used to control the electromechanical device from a power supply. The power supply can be a battery provided to power the apparatus. This provides an easy way of putting the electromechanical device out of action. The control unit can in this case remain connected to the electromechanical device. The H-bridge can be included in the control unit or it might be provided separately. If the H-bridge is included in the control unit, the control unit can also be disconnected from the power supply.

In case a voltage regulator is provided, according to a further alternative, the main control unit is configured to enable and/or disable the output of the voltage regulator providing power to the control unit. The enabling and/or disabling of the output of the voltage regulator can be realized by a switch, for example. In particular, the voltage regulator can be enabled and/or disabled. For instance, the voltage regulator may receive an electrical signal from the main control unit via a control line which enables the output of the voltage regulator, providing power to the control unit or disables the output of the voltage regulator, not providing power to the control unit. Additional voltage regulators may be provided in the system.

An alternative embodiment may also combine the latter alternative with a previous alternative, such that the main control unit controls both a switch and a voltage regulator in order to stop operation of the electromechanical device.

According to a further embodiment of the apparatus according to the invention, the electromechanical device comprises a stepper motor. The control signal for a stepper motor usually provides pulses for discrete steps of the motor, while the amplitude of the current of the control signal only influences the exerted torque or momentum of the stepper motor. A check of the position of the stepper motor and a correction of the position of the stepper motor is thus particularly easy and secure. Moreover, a correlation between a control signal of the control unit and a motion detector signal by the motion detector is facilitated compared to continuously working motors, for example.

The stepper motor can be a unipolar or bipolar stepper motor. The unipolar stepper motor provides a cheap way to achieve precise angular movements, while the bipolar stepper motor is more efficient and powerful. The stepper motor is in particular controlled by means of an H-bridge, which can be a part of the control unit.

If the main control unit is configured to control at least a further element of said apparatus, the apparatus provides an especially efficient and safe system. Generally, the more functions are taken over by the main control unit the more efficient a system can be designed. By still providing a separate control unit in form of a motor driver, for example, the control of the electromechanical device is not compromised by further operations of the main control unit but at the same time a supervision of the control of the electromechanical device is maintained by the main control unit.

Such further elements can in particular be user interface elements like a display, a display controller, buttons and preferably a second control unit.

When the motion detector according to another embodiment of the apparatus according to the invention comprises an optical chopper, an emission source, for example a light source, and at least one detector, a space saving motion detector with low power consumption can be provided. With the optical chopper arranged between the emission source and the detector, the emission source can be alternately covered and uncovered by the mechanical movement of the electromechanical device. This may be realized by one or more flags mounted on a pinion of the electromechanical device or a separate disc having flags such that the flags cover and uncover the detector or the emission source. Of course, the mechanical movement can also be detected at other positions within a drive train, for example. Depending on the number of flags the accuracy of the motion detector can be varied. There may not necessarily be a one-to-one relation between pulses in a control signal and pulses in a motion detector signal. The detector is in this sense an encoder, encoding the mechanical movement or a light signal into an electrical signal. It is in particular preferred to provide two photo detectors as the detector, thus increasing the accuracy with which the movement can be determined. Motion can be deduced by comparing the sates of the two signals of the two photo detectors.

In particular multiple, preferably two, detectors can be used while one emission source is used. Thus a single flag of the chopper can produce four edges in the motion detector signal with one flag passing the detector. Since the there are two detectors and two edges of a flag, this results in four distinguishable signals, when a flag passes the two detectors. This way the resolution of the motion detector can be increased and thus the accuracy and speed of detecting movement of the electromechanical device is improved.

The emission source is preferably a light source like an LED for example, while the detectors are light detectors.

According to another embodiment of the apparatus according to the invention, the apparatus further comprises at least a first reservoir containing a first fluid and a fluidic channel connected at least to the first reservoir. The electromechanical device is configured to exert a pressure at least on the first fluid in the first reservoir such that the fluid is guided through the fluidic channel. It may be problematic to predict and provide the right amount of torque or momentum for the electromechanical device to provide the pressure on the fluid, since the necessary torque depends on multiple factors like the viscosity of the fluid, the diameter of the channel or the ambient temperature, for example. This necessitates a reliable detection of errors and malfunctions. When the main control unit is configured such that information is provided by the main control unit to the control unit and the motion detector and the main control unit are configured such that information about the movement of the electromechanical device is provided by the motion detector at least to the main control unit the reliability of error detections can be improved.

The apparatus may further comprise a second reservoir containing a second fluid and a fluidic channel connected at least to the second reservoir. The electromechanical device is configured such that it can exert a pressure on the second fluid in the second reservoir such that the second fluid is guided through the fluidic channel. In this case it is preferred, that a second electromechanical device and/or a second control unit and/or a second motion detector is provided, as well. In this way two different fluids, in particular drugs or medicaments, can be delivered to the user, preferably independently from each other. The reservoirs are preferably provided in form of exchangeable cartridges.

It is further preferred that the electromechanical device comprises a drive train, wherein said electromechanical device drives said drive train to exert pressure on said first fluid. Such a drive train can include a gearing arrangement and/or a driving rod. This way a rotational movement of the electromechanical device can be transformed into a lateral movement. By providing a gearing arrangement the preciseness can be further improved and the load on the motor can also be influenced to further improve the reliability and power consumption by making the electromechanical device work at an optimal working point, for example. Hence the apparatus can be designed safer in that errors and malfunctions can even be prevented.

Considering the aforementioned electromechanical device, control unit and motion detector as the first electromechanical device, the first control unit and the first motion detector, it is further advantageous, that according to another embodiment of the invention, the apparatus further comprises a second electromechanical device, a second motion detector and optionally a second control unit. The first or - if provided - the second control unit is configured to control the second electromechanical device , wherein the main control unit is configured to provide information to the first or - if provided - to the second control unit. The second motion detector and the main control unit are configured such that information about the movement of the second electromechanical device is provided by the second motion detector at least to the main control unit. In this way a synergetic effect can be utilized of providing independent control units for each electromechanical device but only having to provide a single main control unit in order to significantly improve fail-safety of the apparatus. Of course, it is also possible to provide further control units and/or motion detectors and/or electromechanical devices.

The embodiments of an apparatus comprising only a first electromechanical device, a first motion detector and a first control unit are also applicable to an apparatus comprising further devices and/or detectors and/or units.

According to another embodiment of the invention, a medical device, in particular a portable medical device, for delivering at least one fluid, in particular a drug delivery device, is provided comprising an apparatus according to the invention. In this case the main control unit can send total dosage information to the control unit, which in turn provides the electromechanical device with the corresponding control signal to deliver the dosage by a corresponding mechanical movement. Especially for medical devices, an accurate dose delivery of a certain medicament is of great importance, since over- and under-dosages can be dangerous or even deadly in the worst case. Thus, if a fluid, in particular a medicament or a drug, is delivered by the movement of the electromechanical device, it is important to provide a reliable and predictable movement of the electromechanical device, or - in case of an error - to be aware of any malfunctioning. Especially for a portable medical device, reliable error detection is essential, since they are moved around and especially prone to errors due to jolts, for example.

In particular the medical device is a portable drug delivery device such as a hand-held portable drug delivery device, for example a pen for injecting insulin or an infusion pump.

The technical problem is furthermore solved by a method for operating an apparatus, in particular an apparatus or medical device according to the invention, comprising the steps of providing information from a main control unit to a control unit, controlling an electromechanical device by means of said control unit detecting movement of said electromechanical device and providing information about said movement of said electromechanical device to said main control unit.

The control unit is provided with information, for example with a number of steps the electromechanical device, such as a stepper motor, has to move, or a total dosage which should be dispensed, and thus the control unit can control the electromechanical device independently from the main control unit. At the same time the main control unit is configured to receive information about the movement of the electromechanical device, in particular information from a motion detector or any other kind of sensor. The main control unit can thus observe and check the behaviour of the electromechanical device and / or the control unit. In case of a mismatch between requested and actually executed behavior of either the electromechanical device and/or the control unit, the main control unit can output a warning or intervene and prevent any behavior of the apparatus which might damage the apparatus or harm the user. Such an intervention may be a stop of the electromechanical device, blocking or interrupting a control signal from the control unit, or interrupting the power supply of the electromechanical device, for example.

The control unit and/or the electromechanical device and/or the motion detector can in particular be a first control unit and/or a first electromechanical device and/or a first motion detector, meaning that a second electromechanical device and/or a second motion detector and optionally a second control unit can be provided.

According to an embodiment of the method according to the invention, the method further comprises the step of providing information about said movement of said electromechanical device to said control unit. In case there is only one control unit, information is provided to this control unit, in case there is a first and a second control unit, preferably information about the movement of the first electromechanical device is provided to the first control unit, while information about the movement of the second electromechanical device is provided to the second control unit.

This provides an additional feedback route to prevent malfunctions or any further consequences from a malfunction. The control unit in this case is for example able to perform a comparative operation between the information, for example in form of a control signal, sent to the electromechanical device and the information provided by the motion detector. This is advantageous, since a quick feedback can be provided to the control unit and counter measures correcting the electromechanical device or stopping the electromechanical device can be quickly provided to the electromechanical device without first being processed by the main control unit. At the same time though, the main control unit maintains the ability to overrule instructions by the control unit, for example by disconnecting control unit and electromechanical device, or by suppressing commands from the control unit to the electromechanical device.

In this way a first closed feedback control is provided between control unit, electromechanical device and motion detector. At the same time the second closed feedback between the main control unit, the control unit, the electromechanical device and the motion detector is maintained. This provides a method for an especially safe error detection of an apparatus.

A further advantage of this embodiment is that in case of a software or hardware malfunction either in the sphere of the control unit or in the sphere of the main control unit a corrective action, a preventive action or an intervention of the other unit can be initiated.

It is further preferred that the main control unit compares the information provided from the main control unit to the control unit with the information provided from the motion detector to the main control unit. By a comparison of the information, the main control unit can derive an appropriate action to prevent any damage or harm in case of a mismatch between the information provided to the control unit and the information about the movement of the electromechanical device and thus between the requested movement and the detected movement.

This comparison can be performed while a movement is requested by the electromechanical device, for example. This may save power, since the comparison is not performed permanently. Nevertheless, the comparison can also be performed permanently, even when no movement is requested, to make sure that there is no accidental movement of the electromechanical device. To further reduce power consumption it is also possible to only compare the information when a movement of the electromechanical device is completed.

According to a further embodiment of the method according to the invention, the connection between the control unit and the electromechanical device is interrupted by said main control unit in dependence of said information from said motion detector. The prevention of harmful or damaging consequences can be improved in this way. The interruption can be provided by means of a switch or any sort of electrical or mechanical element able to intervene in the connection between the control unit and the electromechanical device, such as transistors or circuit breakers, for example. This switch can in particular be arranged between the control unit and the electromechanical device in order to easily interrupt the connection there between. Interrupting means that the connection can either be interrupted completely or a connection between the main control unit and the electromechanical device can be established overriding the control unit, for example.

Alternatively, the connection between an H-bridge used to control the electromechanical device and a power supply is interrupted by said main control unit in dependence of said information from said motion detector. The generally more complex connection between the electromechanical device and the control unit can be maintained and the power supply of the H-Bridge, which may also be integrated into the control unit, is interrupted. This provides a particularly reliable way of improving the reliability of the device.

The main control unit may also control at least a further element of said apparatus, in particular a second control unit. A more efficient method can be provided by letting the main control unit control multiple elements, such as displays, buttons, switches or further control units. The control of the electromechanical device is however not compromised by further operations of the main control unit, since the electromechanical devices are controlled by the control units. But at the same time a supervision of the control of the electromechanical device is maintained by the main control unit, still providing improved error detection.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which:

FIG. 4 illustrates another schematic view of the drive mechanism illustrated in

FIG. 3;

FIG. 5a-b illustrate a motion detector that may be used with the drive mechanism illustrated in FIG. 3.

DETAILED DESCRIPTION

Figure 1A:
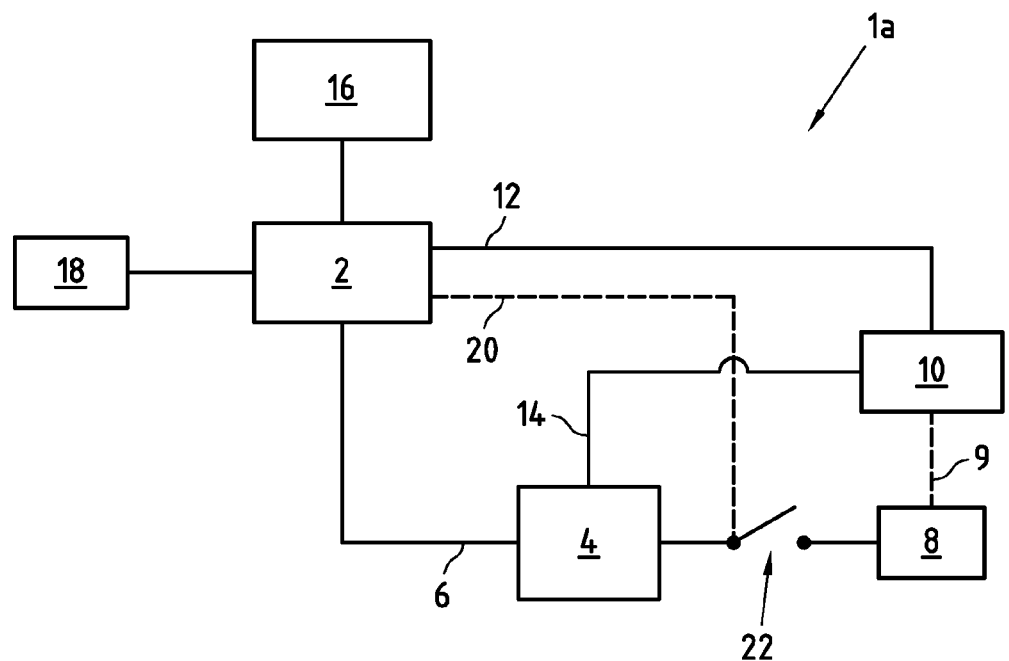
FIG. 1a illustrates a schematic circuit diagram of an exemplary embodiment of an apparatus according to the invention.

FIG. 1a illustrates a schematic circuit diagram 1a of an exemplary embodiment of an apparatus according to the invention. A main control unit 2 is shown, which is connected to a control unit 4 over the connection 6. The main control unit 2 is in particular a microprocessor. The control unit 4 might be logic unit such as a microprocessor or a motor driver. The main control unit 2 provides the control unit 4 with information regarding the control of the electromechanical device 8, which might be a motor and in particular a stepper motor. Connection 6 may be a bidirectional communication between the main control unit 2 and the control unit 4. The elements shown in FIG. 1a can be powered by a battery (not shown), for example.

The mechanical movement of the electromechanical device 8 is detected by the motion detector 10, illustrated by the dotted line 9. This motion detector 10 can in particular be an optical detector comprising an optical chopper, an emission source and a detector to encode the light signal into an electrical signal, which can be processed by the main control unit 2 and/or the control unit 4.

Via a connection 12 and an optional connection 14 the motion detector 10 can provide information about the movement of the electromechanical device 8 to the main control unit 2 and (optionally) the control unit 4. The connection 14 to the control unit may be omitted, for example to reduce implementation costs.

As illustrated in FIG. 1a the main control unit 2 is further connected to user interfaces in form of a display unit 16 and an input element 18, for example one or more buttons or a touch screen. Over the input element 18 the user can provide the main control unit 2 with information how to control the control unit 4 such as a specific dosage of a medicament, for example. Via the display unit the user might check the input information, before confirming the input.

The main control unit 2 can then provide information to the control unit 4 over the connection 6. The control unit 4 provides corresponding information to the electromechanical device, such as a control signal, in order to trigger a corresponding movement of the electromechanical device 8. The motion detector 10 then provides information to the main control unit 2 about the movement of the electromechanical device 8.

In case there is a mismatch between the information provided to the control unit 4 by the main control unit and the information provided by the motion detector 10, the main control unit 2 may react accordingly. This means that the control unit can for example inform the user of the error over the display unit 16. The main control unit 4 may also send further information to the control unit 4 in order to counterbalance the mismatch. This works, for example, if the motor only performed a smaller movement than requested. In case the apparatus is used in a medical device, this may prevent an underdose, example. The main control unit 2 may also interrupt the connection between the control unit 4 and the electromechanical device 8 via the connection 20, illustrated by the dotted line.

A switch 22 is located between the control unit 4 and the electromechanical device 8. This switch is illustrated in the open position. Of course, when the control unit 4 provides information to the electromechanical device, this switch 22 needs to be closed. Thus, in the normal case the switch 22 is closed. In case of an error or a malfunction, for example of the electromechanical device 8 or the control unit 4, the main control unit 2 can trigger the switch 22 to stop the mechanical device 8 from further receiving information from the control unit 4 and thus preventing the electromechanical device 8 from further movement. In case the apparatus is used in a medical device, this might prevent an overdose, for example. The switch can comprise a transistor for electronic switching, for example, but a mechanical switch is possible as well.

Alternatively, the main control unit 2 could also override the control signals of the control unit 4 and provide information to the electromechanical device 8 itself.

The optional connection 14 can also be used to receive information from the motion detector 10, so that an error can also be detected by the control unit 4. In this way, a faster error detection might be realized, though the main control unit 2 has still the possibility of overruling the control unit 4.

Figure 1B:
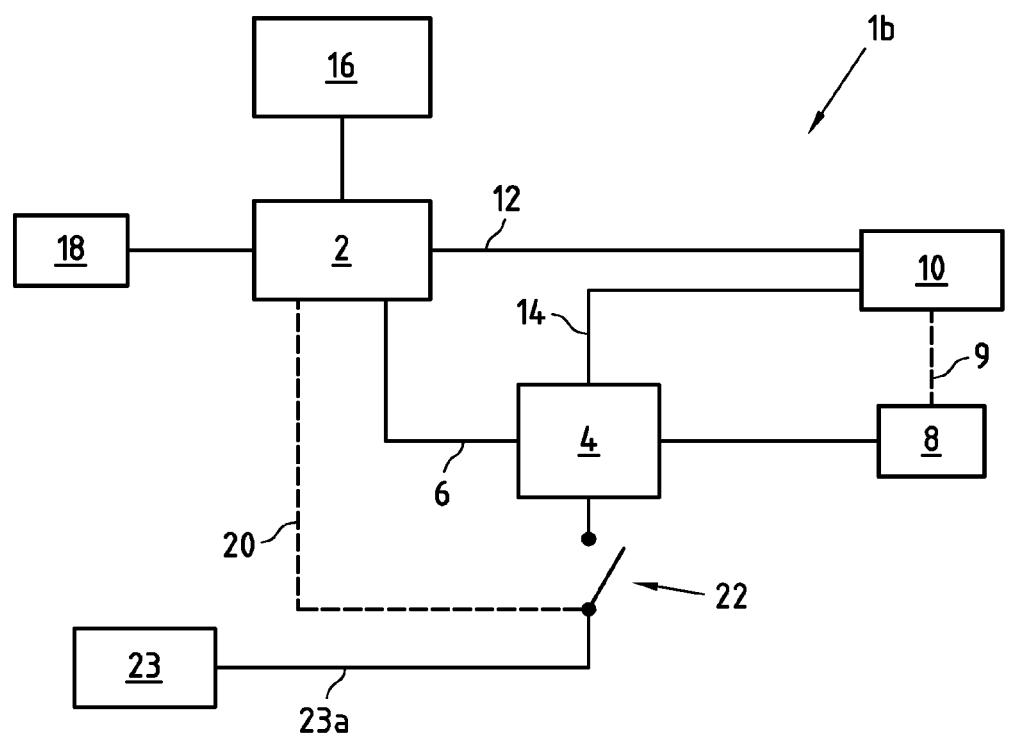
FIG. 1b illustrates a schematic circuit diagram of a further exemplary embodiment of an apparatus according to the invention.

FIG. 1b illustrates a schematic circuit diagram 1b of a further exemplary embodiment of an apparatus according to the invention. The illustrated schematic circuit diagram 1b is similar to the one illustrated in FIG. 1a. It differs from the schematic circuit diagram 1a in that the main control unit 2 operates the switch 22 in order to disconnect the H-bridge included in the control unit 4 from the power supply 23 to which the control unit 4 is connected over the connection 23a. The power supply 23 also provides power to the further elements, such as the main control unit 2, the display unit 16, the electromechanical device 8 and/or the motion detector 10, even though no connections are illustrated. It is also possible to disconnect only the connection of the power supply 23 to the H-bridge, without disconnection the control unit 4 completely.

Figure 1C:
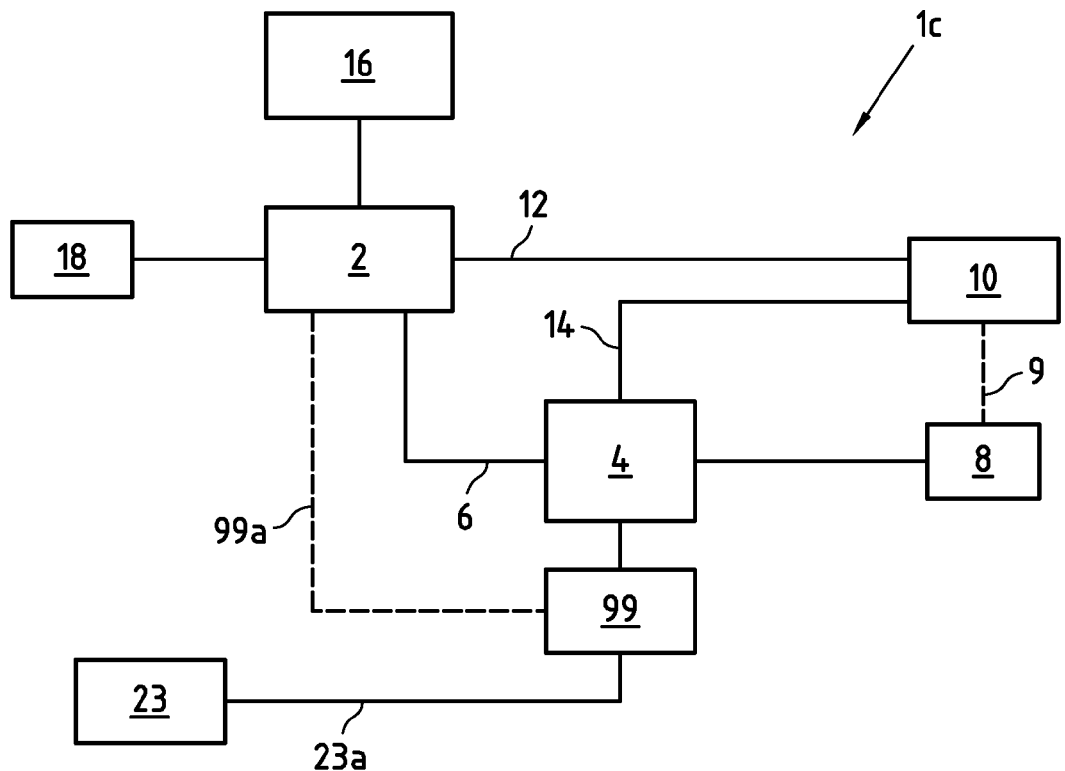
FIG. 1c illustrates a schematic circuit diagram of a further exemplary embodiment of an apparatus according to the invention.

FIG. 1c illustrates a schematic circuit diagram 1c of a further exemplary embodiment of an apparatus according to the invention. The illustrated schematic circuit diagram 1c is similar to the one illustrated in FIG. 1b. It differs from the schematic circuit diagram 1b in that a voltage regulator 99 converts the voltage from the power supply 23 to a voltage suitable for use by the control unit 4. This voltage regulator 99 receives an electrical signal from the main control unit 2 via a control line 99a which enables the output of the voltage regulator 99, providing power to the control unit 4 or disables the output of the voltage regulator 99, not providing power to the control unit 4. There may be additional voltage regulators in the system which are not shown in the schematic for clarity.

An alternative embodiment may combine the mechanisms shown in FIG. 1b and FIG. 1c, such that the main control unit 2 controls both a switch 22 and a voltage regulator 99 in order to stop operation of the electromechanical device.

Figure 2:
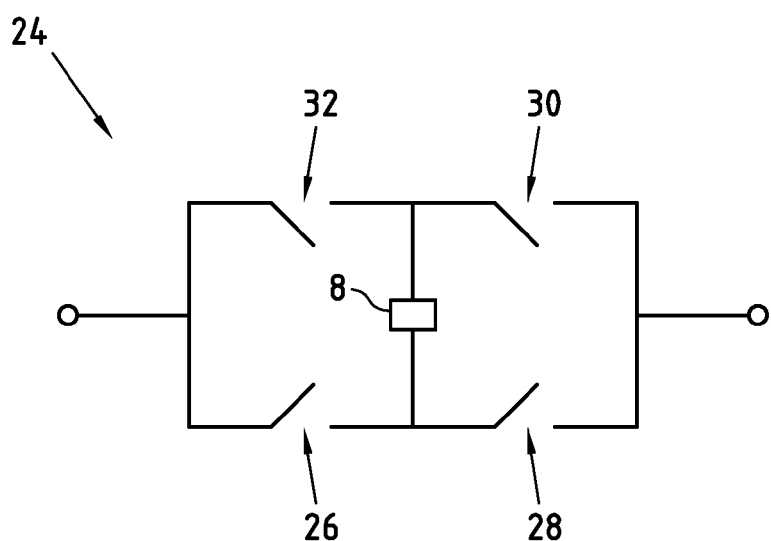
FIG. 2 illustrates a schematic circuit diagram of an H-bridge.

FIG. 2 illustrates a schematic circuit diagram of an H-bridge 24. The H-bridge 24 might be used to control the electromechanical device 8, in particular a bipolar stepper motor or dc-motor. The H-bridge 24 comprises four switches 26, 28, 30, 32. By closing switches 26 and 30 the voltage will be applied across the electromechanical device opposite to the direction when switches 28 and 32 are closed. This way a bipolar stepper motor, which is efficient and powerful, can be used or a dc-motor can be driven forward and backward to counteract any detected errors, for example.

In the following figures components of a drug delivery device for the delivery of two drugs are described. The use of an apparatus and a method according to the invention is especially advantageous in such medical devices, since an accurate dose delivery of a certain medicament or drug is of great importance, since over and under dosages can be deadly in the worst case. Thus, if a fluid, in particular a medicament or a drug, is delivered by the movement of the electromechanical device 8, it is important to provide a reliable and predictable movement of the electromechanical device 8.

Figure 3:
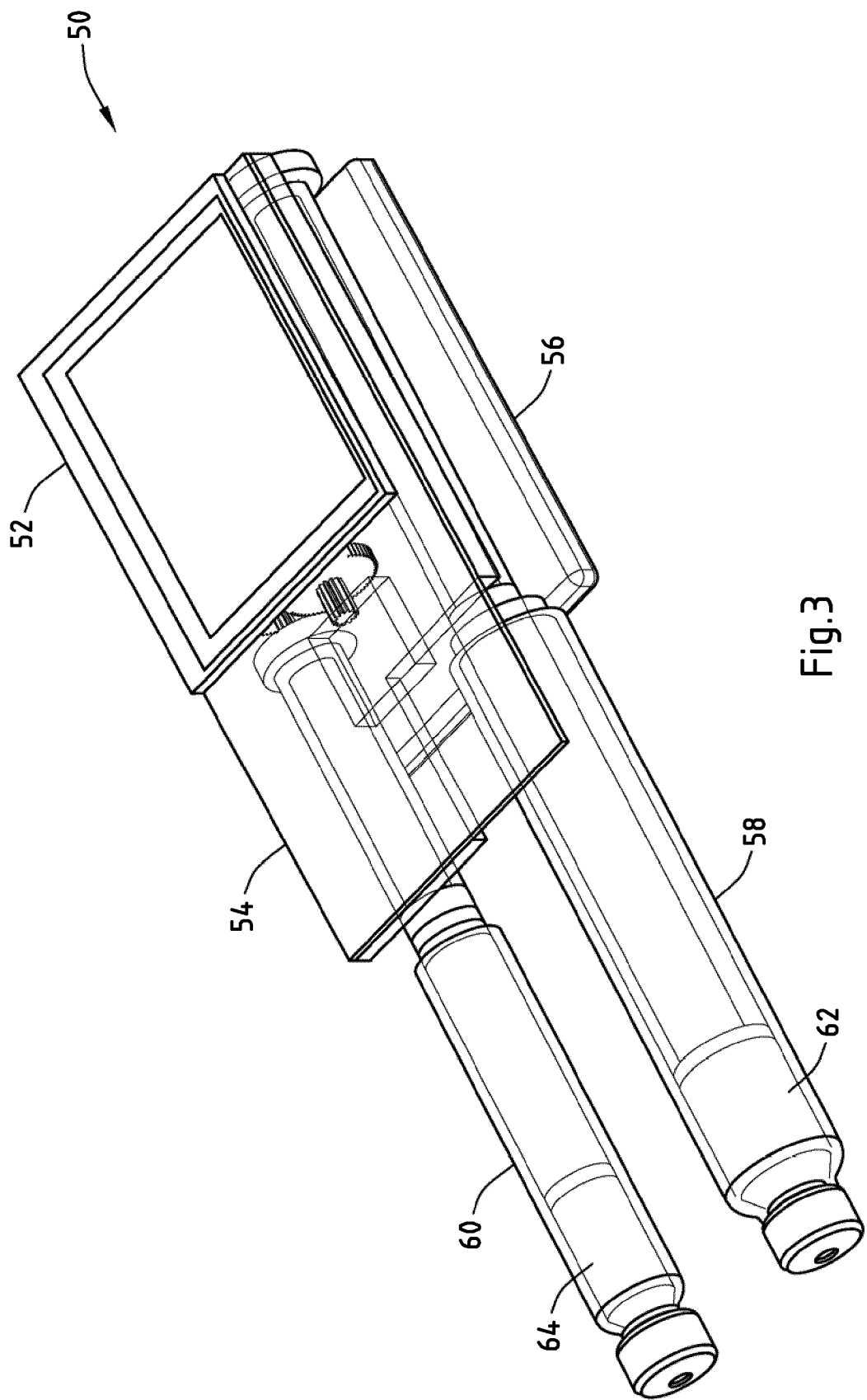
FIG. 3 illustrates a schematic view of a drive mechanism for use with a drug delivery system.

FIG. 3 illustrates various internal components of a drug delivery device including one preferred arrangement of a drive train 50. FIG. 3 also illustrates a digital display 52, a printed circuit board assembly (PCBA) 54, along with a power source or battery 56. The PCBA 54 may be positioned between the digital display 52 and a drive train 50 with the battery or power source 56 positioned beneath this drive train 50. The battery or power source 52 is electronically connected to provide power to the digital display 52, the PCBA 54 and the drive train 50. As illustrated, both a first and second cartridges 58, 60 are shown in an expended state. That is, the first and second cartridges are illustrated in an empty state having a stopper 62, 64 at a most distal position. For example, the first cartridge 58 (which ordinarily contains a first medicament) is illustrated as having its stopper 62 in the distal position. The stopper 64 of the second cartridge 60 (ordinarily containing the second medicament) is illustrated in a similar position.

With reference to FIG. 3, it may be seen that there is provided a first region defining a suitable location for a power source 56 such as a replaceable battery or batteries. The power source 56 may comprise a rechargeable power source and may be recharged while the power source 56 remains in the device. Alternatively, the power source 56 may be removed from the drug delivery device and recharged externally, for example, by way of a remote battery charger. This power source may comprise a Lithium-Ion or Lithium-polymer power source. In this preferred arrangement, the battery 56 comprises a generally flat and rectangular shaped power source.

Figure 4:
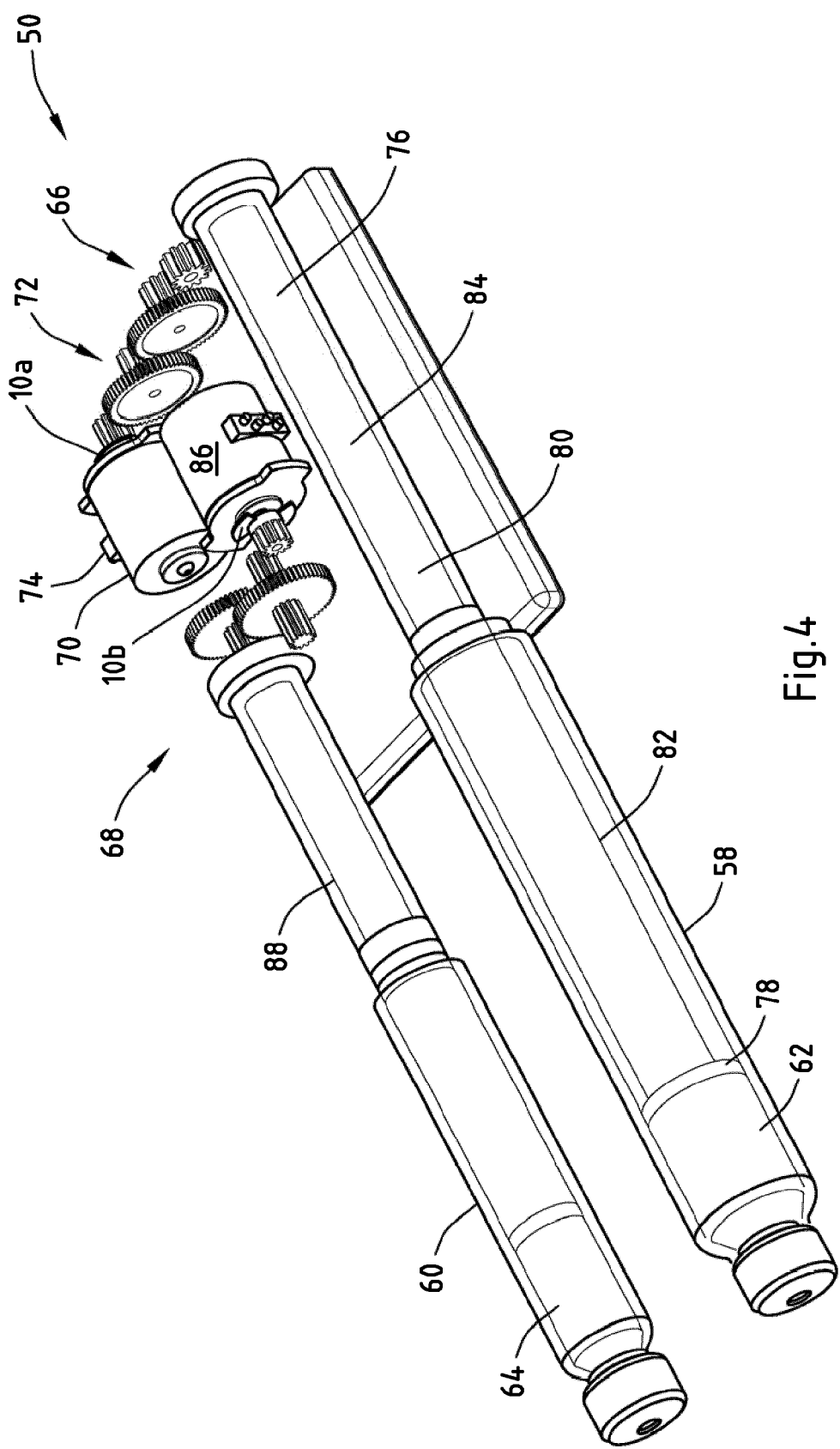

FIG. 4 illustrates the arrangement of the electro-mechanical system illustrated in FIG. 3 with both the digital display 52 and the PCBA 54 omitted. As illustrated in FIG. 4, the drive train 50 operates to expel a dose from the first cartridge 58 containing the primary medicament and the second cartridge 60 containing the secondary medicament. Again, as illustrated in FIG. 7, the first and second cartridges 58, 60 are illustrated in an empty state having stoppers at a most distal position.

In this preferred drive train 50, the system comprises an independent electromechanical device 8 in form of motors 70, 86 for each cartridge 58, 60. That is, an independent mechanical driver 66 operates to expel a dose from the first cartridge 58 and an independent mechanical driver 68 operates to expel a dose from the second cartridge 60. In an alternative drive train 50 operating on three different medicaments, three independent mechanical drivers could be provided. The independent mechanical drivers can act under control of motor drivers of a control unit 4 (see FIG. 1*a*).

The first independent mechanical driver 66 operates to expel a dose from the first cartridge 58. This first driver 66 comprises a first electromechanical device 8 in form of a motor 70 that is operatively coupled to a first gearing arrangement 72. To energize this motor 70, a connector 74 is provided as a means of electrically connecting to the motor driver. This first gearing arrangement 72 is mechanically linked to a proximal portion of the first telescoping piston rod 76. The first telescoping piston rod 76 is illustrated in a fully extended position having a distal end 78 acting on the stopper 62 of the first cartridge 58.

As this gearing arrangement 72 is driven by the output shaft of the first motor 70, this arrangement 72 rotates the proximal portion 80 of the first telescoping piston rod 76. As this proximal portion 80 of the piston rod 76 is rotated, the second or distal portion 82 of the piston rod 76 is driven in a distal direction.

Preferably, the proximal portion 80 of the telescope piston rod 76 comprises an external thread 84. This thread 84 engages the distal portion 82 which has in integrated nut comprising a short threaded section at a proximal end of the distal portion 82. This distal portion 82 is prevented from rotating via a key acting in a keyway. Such a keyway may pass through the middle of first telescope 76. Therefore, when the first gearbox arrangement 72 causes rotation of the proximal section 80, rotation of the proximal portion 80 acts upon the distal end 78 to thereby drive the distal portion of telescope piston rod to extend along the longitudinal axis.

Moving in this distal direction, the distal end 78 of the second portion 82 of the piston rod 76 exerts a force on a stopper 62 contained within the first cartridge 58. With this distal end 78 of the piston rod 76 exerting a force on the stopper, the user selected dose of the first medicament is forced out of the cartridge 58 and into an attached dispense interface, for example, and then out an attached needle assembly which can allow the user to inject the medicament.

A similar injection operation occurs with the second independent driver 68 when a controller first determines that a dose of a second medicament is called for and determines the amount of this dose. In certain circumstances, the controller may determine that a dose of the second medicament may not be called for and therefore this second dose would be "set" to a "0" dose.

Preferably, motors 70, 86 comprise motors suitable for electronic commutation. Most preferably, such motors may comprise either a stepper motor or a brushless DC motor.

To inject a dose of the primary and secondary medicaments a user will first select a dose of the primary medicament by way of the human interface components on the display 52 (see FIG. 3).

When the dose sizes of the first and second medicaments have been established, the motor drivers energize both the first and the second motors 70, 86 to begin the injection process described above.

The piston rods 76, 88 are preferably movable between a first fully withdrawn position (not shown) and a second fully extended portion (as shown in FIGS. 6 and 7). With the piston rods 76, 88 in the withdrawn position, the user will be allowed to open up the respective cartridge retainer and remove an empty cartridge.

In one preferred arrangement, both the first and second motors 70, 86 operate simultaneously so as to dispense the user selected dose of the first medicament and the subsequently calculated dose of the second medicament simultaneously. That is, both the first and the second independent mechanical drivers 66, 68 are capable of driving the respective piston rods 76, 88 either at the same or a different time.

One or more of the steps of the injection may be performed automatically, for example controlled by a microcontroller, for example by the control unit 4 or the main control unit 2, such as the step of rewinding the first and/or second piston rod. In an alternative arrangement, the microcontroller, in particular the main control unit 2, may be programmed so that the first and the second independent mechanical drivers 66, 68 may be operated to dispense either the first medicament or the second medicament prior to the other medicament. Thereafter, the second or the primary medicament may then be dispensed. In one preferred arrangement, the secondary medicament is dispensed before the primary medicament.

Preferably both motors 70, 86 may be operated in a reverse direction. This feature may be required in order to allow the piston rods 76, 88 to be moved between a first and a second position.

The first independent mechanical driver 66 illustrated in FIG. 4 comprises a first motion detector 10a. FIG. 5*a* illustrates a perspective view of the first motor 70 illustrated in FIG. 4. FIG. 5*b* illustrates a preferred motion detector 10a comprising the first motor 70 illustrated in FIG. 5*a* in conjunction with a detector in form of a digital encoder 90.

As illustrated in FIGS. 5*a* and 5*b*, such a motion detector 10a may is beneficial as it is utilized to provide operational and positional feedback from the first independent driver 66 to the main control unit 2 or the control unit 4 of the drug delivery device. For example, with respect to the first independent driver 66, a preferred motion detector 10a is achieved through the use of a first motor pinion 92. This first pinion 92 operatively coupled to an output shaft 94 of the first motor 70. The first pinion 92 comprises a rotating gearing portion 96 that drives a first gear of the first gearing arrangement 72 (see, e.g., FIG. 7). The first motor pinion 92 also comprises a plurality of flags 98 a-b. In this first motion detector 10a, the first pinion 92 comprises a first flag 98*a* and a second flag 98*b*. These two flags 98*a-b* are positioned on the motor pinion 92 so that they pass through a first optical encoder 90 as the motor output shaft 94 and hence the connected first pinion 92 rotate when the motor is driven.

Preferably, as the first and second flags 98a-b pass through the first optical encoder 90, the encoder 90 can send certain electrical pulses to a microcontroller, for example the main control unit 2 or the control unit 4. Preferably, the optical encoder 90 sends two electrical pulses per motor output shaft revolution to the microcontroller. As such, the microcontroller can therefore monitor motor output shaft rotation. This is advantageous to detect position errors or events that could occur during a dose administration step such as jamming of the drive train, incorrect mounting of a dispense interface or a needle assembly, or where there is a blocked needle.

In order to increase the accuracy of the motion detection, it is particularly preferred to provide more than two flags on the motor pinion 92. In combination with a motion detector including two photo detectors, multiple positions during a revolution of motor output shaft can be distinguished, since 4 positions of a flag are registered (both photo detectors, the first photo detector, the second photo detector or none of the photo detectors detect light). With five flags 20 positions during a revolution of motor output shaft can be distinguished.

Preferably, the first pinion 92 comprises a plastic injection molded pinion. Such a plastic injection molded part may be attached to the output motor shaft 94. The optical encoder 90 may be located and attached to a gearbox housing. Such a housing may contain both the first gearing arrangement 72 along with the optical encoder 90. The encoder 90 is preferably in electrical communication with the main control unit 2 potentially via a flexible portion of the PCB. In a preferred arrangement, the second independent mechanical driver 68 illustrated in FIGS. 3 and 4 comprises a second motion detector 10b that operates in a similar and preferably in the same fashion as the first motion detector 10a of the first mechanical driver 66.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. Apparatus comprising: an electromechanical device, a control unit, a main control unit and a motion detector, wherein said control unit is configured to control said electromechanical device, and wherein said electromechanical device is a motor, characterized in that said control unit and said main control unit are realized with microprocessors, said main control unit is configured to provide information to said control unit, and said motion detector and said main control unit are configured such that information about the movement of said electromechanical device is provided by said motion detector at least to said main control unit, wherein said main control unit is configured to provide information regarding control of the electromechanical device to said control unit, and said control unit is configured to provide a corresponding control signal to said electromechanical device to control said electromechanical device, wherein said motion detector and said main control unit are configured such that the information about the movement of said electromechanical device is provided by said motion detector to said main control unit and said control unit.

2. Apparatus according to claim 1, wherein said motion detector is configured to provide the information to said control unit.

3. Apparatus according to claim 1, wherein the main control unit is configured to control a switch to disconnect the control unit from the electromechanical device.

4. Apparatus according to claim 1, wherein the main control unit is configured to control a switch to disconnect an H-bridge used to control the electromechanical device from a power supply.

5. Apparatus according to claim 1, wherein the main control unit is configured to enable and/or disable the output of a voltage regulator providing power to the control unit.

6. Apparatus according to claim 1, wherein said electromechanical device comprises a stepper motor.

7. Apparatus according to claim 1, wherein said main control unit is configured to control at least a further element of said apparatus.

8. Apparatus according to claim 1, wherein said motion detector comprises an optical chopper, an emission source and at least one detector.

9. Apparatus according to claim 1, further comprising
at least a first reservoir containing a first fluid, and
a fluidic channel connected at least to said first reservoir, wherein said electromechanical device is configured to exert a pressure at least on said first fluid in said first reservoir such that said fluid is guided through said fluidic channel.

10. Apparatus according to claim 1, further comprising a drive train, wherein said electromechanical device drives said drive train to exert pressure on said first fluid.

11. Apparatus according to claim 1, further comprising:
a second electromechanical device,
a second motion detector,
wherein said control unit is configured to control said second electromechanical device,
wherein said main control unit is configured to provide to said control unit and
wherein said second motion detector and said main control unit are configured such that information about the movement of second electromechanical device is provided by said second motion detector at least to said main control unit.

12. Medical device, in particular a portable medical device, for delivering at least one fluid, in particular a drug delivery device, comprising an apparatus according to claim 1.

13. Method for operating an apparatus, in particular an apparatus or medical device according to claim 1, comprising the steps of
providing information from a main control unit to a control unit, wherein said control unit and said main control unit are realized with microprocessors,
controlling an electromechanical device by means of said control unit, wherein said electromechanical device is a motor,
detecting movement of said electromechanical device, and
providing information about said movement of said electromechanical device to said main control unit.

14. Method according to claim 13, further comprising the step of
providing information about said movement of said electromechanical device to said control unit.

15. Method according to claim 13, wherein said main control unit compares the information provided from said main control unit to said control unit with said information provided from said motion detector to said main control unit.

16. Method according to claim 13, wherein the connection between an H-bridge used to control the electromechanical device and a power supply is interrupted by said main control unit in dependence of said information from said motion detector.

17. Apparatus according to claim 1, wherein said control unit is configured to perform a comparative operation between the control signal sent to said electromechanical device and the information about the movement of said electromechanical device, and wherein said main control unit is configured to compare the information provided by the main control unit with the information about the movement of said electromechanical device, and, in the case of a mismatch between the information provided by the main control unit and the information about the movement of said electromechanical device, said main control unit is configured to overrule the control signal provided by the control unit.

18. A medical device for delivering at least one fluid, said medical device comprising:
an electromechanical device, wherein said electromechanical device is a motor,
a control unit,
a main control unit and
a motion detector,
wherein:

said control unit and said main control unit are realized with microprocessors, said main control unit is configured to provide information regarding control of the electromechanical device to said control unit, and said control unit is configured to provide a corresponding control signal to said electromechanical device to control said electromechanical device, said motion detector and said main control unit are configured such that information about the movement of said electromechanical device is provided by said motion detector to said main control unit and said control unit, said control unit is configured to perform a comparative operation between the control signal sent to said electromechanical device and the information about the movement of said electromechanical device, and said main control unit is configured to compare the information provided by the main control unit with the information about the movement of said electromechanical device, and, in the case of a mismatch between the information provided by the main control unit and the information about the movement of said electromechanical device, said main control unit is configured to overrule the control signal provided by the control unit.

* * * * *